US012390239B2

(12) United States Patent
Ateshian et al.

(10) Patent No.: US 12,390,239 B2
(45) Date of Patent: Aug. 19, 2025

(54) SYSTEMS AND APPARATUSES FOR MANIPULATING BENDABLE ALLOGRAFTS

(71) Applicant: THE TRUSTEES OF COLUMBIA UNIVERSITY IN THE CITY OF NEW YORK, New York, NY (US)

(72) Inventors: Gerard Agop Ateshian, New York, NY (US); Brandon Kendrick Zimmerman, Narvon, PA (US); Courtney Adair Petersen, Holladay, UT (US); Melvin P. Rosenwasser, Palisades, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1035 days.

(21) Appl. No.: 17/235,899

(22) Filed: Apr. 20, 2021

(65) Prior Publication Data

US 2021/0298780 A1    Sep. 30, 2021

Related U.S. Application Data

(63) Continuation of application No. PCT/US2019/057363, filed on Oct. 22, 2019.

(60) Provisional application No. 62/748,917, filed on Oct. 22, 2018.

(51) Int. Cl.
| | |
|---|---|
| *A61B 17/28* | (2006.01) |
| *A61B 17/00* | (2006.01) |
| *A61B 17/29* | (2006.01) |
| *A61F 2/46* | (2006.01) |

(52) U.S. Cl.
CPC ........ *A61B 17/2812* (2013.01); *A61B 17/282* (2013.01); *A61B 2017/00433* (2013.01); *A61B 2017/2808* (2013.01); *A61B 17/2909* (2013.01); *A61B 2017/2911* (2013.01); *A61B 2017/2937* (2013.01); *A61B 2017/2939* (2013.01); *A61B 2017/2947* (2013.01); *A61F 2/4601* (2013.01); *A61F 2002/4622* (2013.01)

(58) Field of Classification Search
CPC ............ A61B 17/0482; A61B 17/0483; A61B 17/0625; A61B 17/128; A61B 17/1796; A61B 17/885; A61B 17/2804; A61B 17/2812; A61B 17/282; A61B 17/30; A61B 2017/2926; A61F 2/4601; A61F 2/4611; A61F 2/4618
See application file for complete search history.

(56) References Cited

U.S. PATENT DOCUMENTS

| | | | | | |
|---|---|---|---|---|---|
| 3,349,772 | A | * | 10/1967 | Rygg | A61B 17/04 D24/143 |
| 4,224,947 | A | * | 9/1980 | Fukuda | A61B 17/04 606/167 |
| 5,454,823 | A | * | 10/1995 | Richardson | A61B 17/282 606/147 |

(Continued)

OTHER PUBLICATIONS

Written Opinion of the International Searching Authority of PCT App. No. PCT/US2019/057363 mailed Dec. 31, 2019.

*Primary Examiner* — Sarah W Aleman
(74) *Attorney, Agent, or Firm* — BakerHostetler

(57) ABSTRACT

A Surgical forceps device comprising a pair of shanks and a clamping jaw portion, the clamping jaw surfaces set at an angle that produces a desired angular position for grasping a bendable osteochondral allograft.

12 Claims, 25 Drawing Sheets

(56) References Cited

U.S. PATENT DOCUMENTS

| | | | |
|---|---|---|---|
| 6,579,304 B1 | 6/2003 | Hart et al. | |
| 6,638,283 B2 * | 10/2003 | Thal | A61B 17/0469 |
| | | | 606/144 |
| 9,017,372 B2 | 4/2015 | Artale et al. | |
| 9,655,672 B2 | 5/2017 | Artale et al. | |
| 10,376,277 B2 | 8/2019 | Dam-Huisman et al. | |
| 2008/0082121 A1 * | 4/2008 | Chu | A61F 2/0045 |
| | | | 606/1 |
| 2018/0325580 A1 | 11/2018 | Sims et al. | |

* cited by examiner

SYSTEMS AND APPARATUSES FOR MANIPULATING BENDABLE ALLOGRAFTS

CROSS-REFERENCE TO RELATED APPLICATIONS

The present application is a continuation of PCT/US2019/057363 filed Oct. 22, 2019, which claims priority to U.S. Provisional Application 62/748,917, filed Oct. 22, 2018, the entirety of which are incorporated herein by reference.

STATEMENT OF GOVERNMENT INTEREST

The invention was made with government support under 1144155, awarded by the National Science Foundation. The government has certain rights in the invention.

FIELD

Systems and apparatuses including surgical forceps device for manipulating a bendable osteochondral allograft.

BACKGROUND

Osteochondral grafting is a method of treating cartilage injuries that expose underlying bone. Osteochondral allografts replace both the articular cartilage on the surface and the underlying bone. Donor tissue must be adapted to match the patient, and as such these allografts typically need to be bent, trimmed, and clamped during the procedure by hand, without interference from wires or screws inserted to secure the allograft in its bent shape. However, surgical instruments lack the ability to effectively guide fixation of allografts, allow proper alignment for trimming and handling, and firmly secure the allograft, thereby introducing difficulties during surgery.

What is needed is a surgical device and system, and in particular, forceps capable of effectively aligning, and allowing for trimming and handling of a bendable allograft during surgery without interference of wires and screws.

SUMMARY

In one aspect, a surgical clamp system is provided. A surgical clamp system, includes a forceps device having first and second shanks, each shank including a distal jaw portion having an inwardly facing surface and an outwardly facing surface. The first and second shanks are configured to pivot between open and closed configurations, wherein the distal jaw portions are disposed in adjacent relationship in the closed configuration. The jaw portion of the second shank defining an opening therethrough from said inwardly facing surface to said outwardly facing surface. A tubular member is provided having first and second opposing ends and a lumen therethrough for receiving a guidewire, wherein the second end of the tubular member includes an outer diameter configured to be received within the opening in the second shank.

In some embodiments, the distal jaw portion of the first shank defines an opening therethrough.

In some embodiments, the surgical clamp system further includes a guidewire, wherein the tubular member is at least partially received within the opening of the second shank and the first opposing end of the tubular member extends outwardly away from the second shank, and the guidewire is received in the lumen.

In another aspect, a surgical forceps device is provided which includes a pair of shanks each defining a distal jaw portion, a proximal portion and a length therebetween and being pivotally interconnected at a position between the distal and proximal portions and movable through respective parallel planes between a closed position at which the respective distal jaw portions are disposed in adjacent relationship and an open position at which the respective distal ends are disposed in a spaced apart relationship from each other. The jaw portions define a clamping jaw, each of the jaw portions includes a polygonal body, the polygonal body of each respective jaw portion having a respective outwardly facing surface and a respective inwardly facing tapered surface.

In some embodiments, the respective axis of the respective clamping jaws are offset from the central axis of the forceps device.

In some embodiments, at least one of the jaw portions includes an opening formed therein, the opening extending along the width of the respective jaw portion. In some embodiments, the opening is an elongated slot extending partially along a length of at least one of the jaw portions. In some embodiments, the opening is a circular hole extending through at least one of the jaw portions along the width of the jaw portion. In some embodiments, the respective inwardly facing tapered surface of the jaw portion associated with the first shank opposes the respective inwardly facing tapered surface of the jaw portion associated with the second shank. In some embodiments, the respective inwardly tapered surface extends away from the respective outwardly facing surface at an angle. In some embodiments, the angle with respect to the rotation axis is about 20 degrees.

In some embodiments, the inwardly facing tapered surface includes a textured surface. In some embodiments, the textured surface includes a serrated or knurled surface.

In some embodiments, the first and second shanks pivot about a rotation axis, and wherein each distal jaw portion is bent in a plane orthogonal to the rotation axis. In some embodiments, the first and second shanks pivot about a rotation axis, and wherein each distal jaw portion is bent out of the plane orthogonal to the rotation axis of the main pivot joint.

In some embodiments, each distal jaw portion is fixed with respect to its respective shank. In some embodiments, each distal jaw portion is pivotally mounted with respect to its respective shank. In some embodiments, a positioning mechanism to maintain a parallel relationship of the first and second distal jaw portions.

In some embodiments, the proximal portion of each of the shanks is shaped to receive a finger or thumb of a person operating the forceps. In some embodiments, the adjacent clamping jaws of the shanks are configured to receive a bendable allograft.

In another aspect, a surgical forceps device is provided, including a pair of shanks each including a distal jaw portion, a proximal portion and a length therebetween and being pivotally interconnected about a first pivot point at a position between the distal and proximal portions and movable through respective parallel planes between a closed position at which the respective distal jaw portions are disposed in adjacent relationship to each other, and an open position at which the respective distal jaw portions are disposed in a spaced apart relationship from each other. The distal jaw portions define a distal jaw, each of the jaw portions including a polygonal body along the respective axis, the polygonal body of each respective jaw portions having a respective outwardly facing surface, which may be tapered, and a respective inwardly facing tapered surface. A positioning mechanism is operatively engaged to the pair of shanks, the positioning mechanism is configured to maintain a parallel alignment of the jaw portions.

In some embodiments, each jaw portion is pivotally mounted to each respective shank, and each jaw portion defines a longitudinal slot extending along a length of said jaw portion, and the positioning mechanism includes a first link and a second link, each link having first and second ends, wherein the first end of a respective link is secured to a respective jaw portion, and the second end of respective links is configured to translate in the slot disposed along a length of the opposite jaw portion. In some embodiments, the first link is connected to the second link at a second pivot point. In some embodiments, the second pivot point is aligned along a central axis of the surgical forceps. The second pivot point maintains alignment along the central axis of the surgical forceps irrespective of the open and closed positions of the shanks.

In some embodiments, a saw blade guide slot is disposed at a distal end of each jaw portion. In some embodiments, the saw blade guide slots are aligned with each other. In some embodiments, a locking mechanism is included to prevent the jaw portions from moving away from each other These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a," "an," and "the" include plural referents unless the context clearly dictates otherwise.

BRIEF DESCRIPTION OF THE DRAWINGS AND FIGURES

The disclosed aspects will hereinafter be described in conjunction with the appended drawings, provided to illustrate and not to limit the disclosed aspects, wherein like designations denote like elements.

Figure 1A:
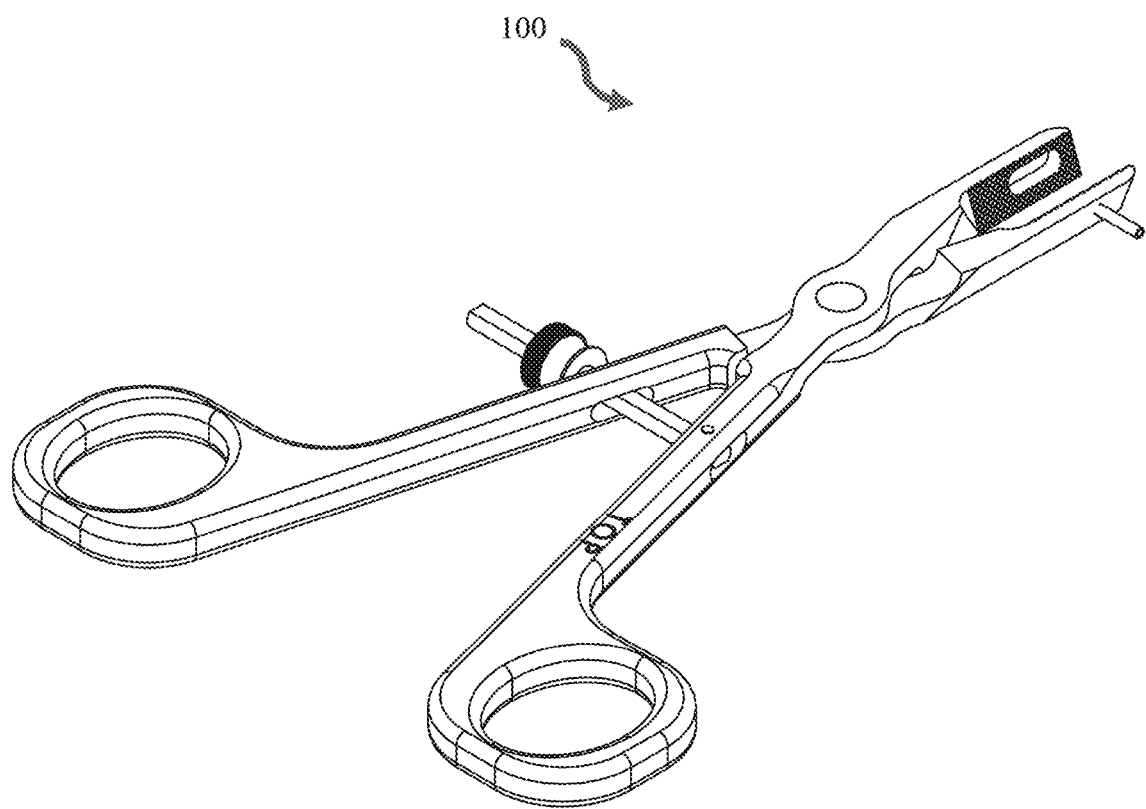
FIG. 1A is a perspective schematic diagram of the surgical forceps device according to an exemplary embodiment.
Figure 1B:
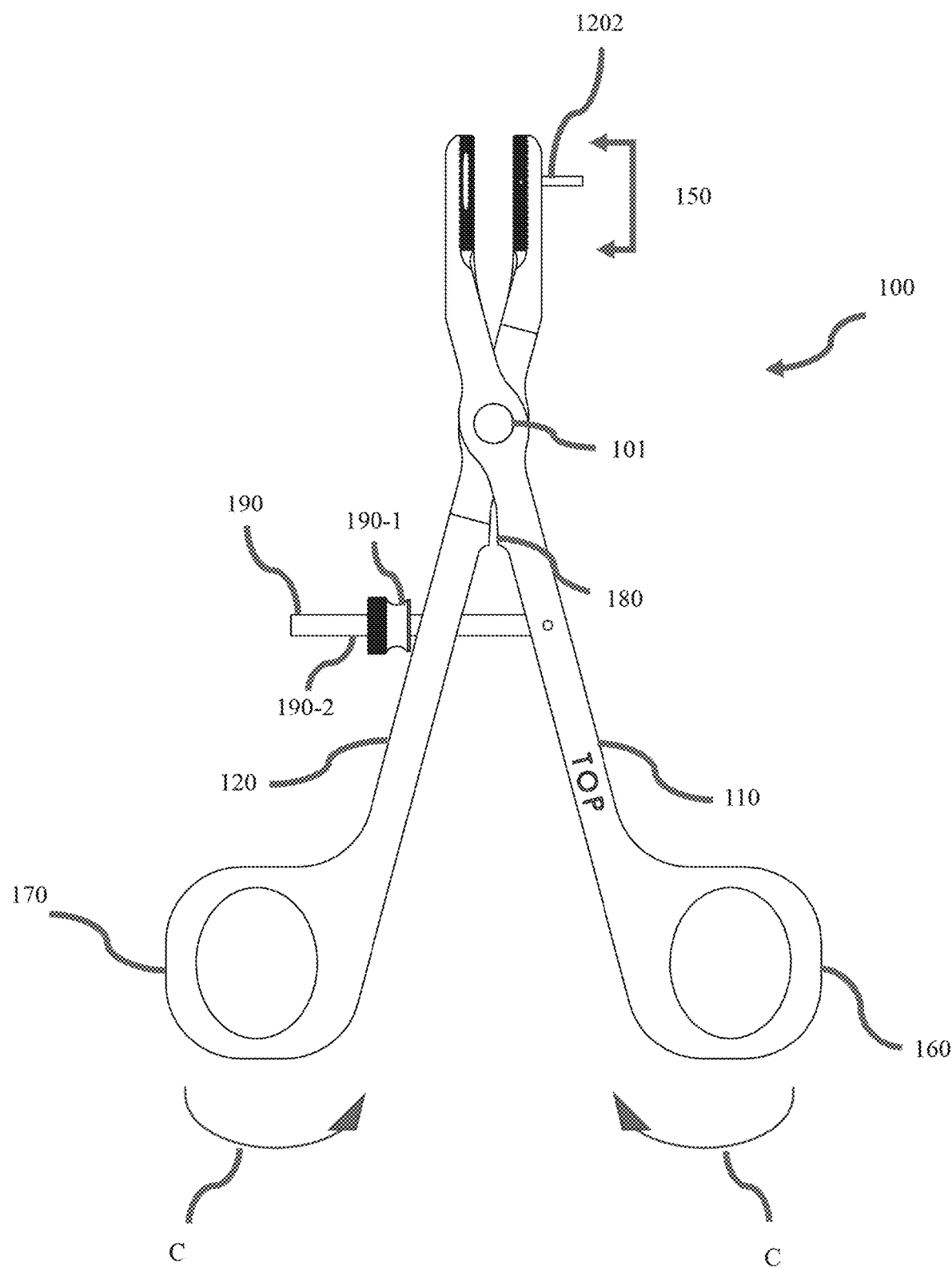
FIG. 1B is a top view of the surgical forceps device as shown in FIG. 1A.
Figure 1C:
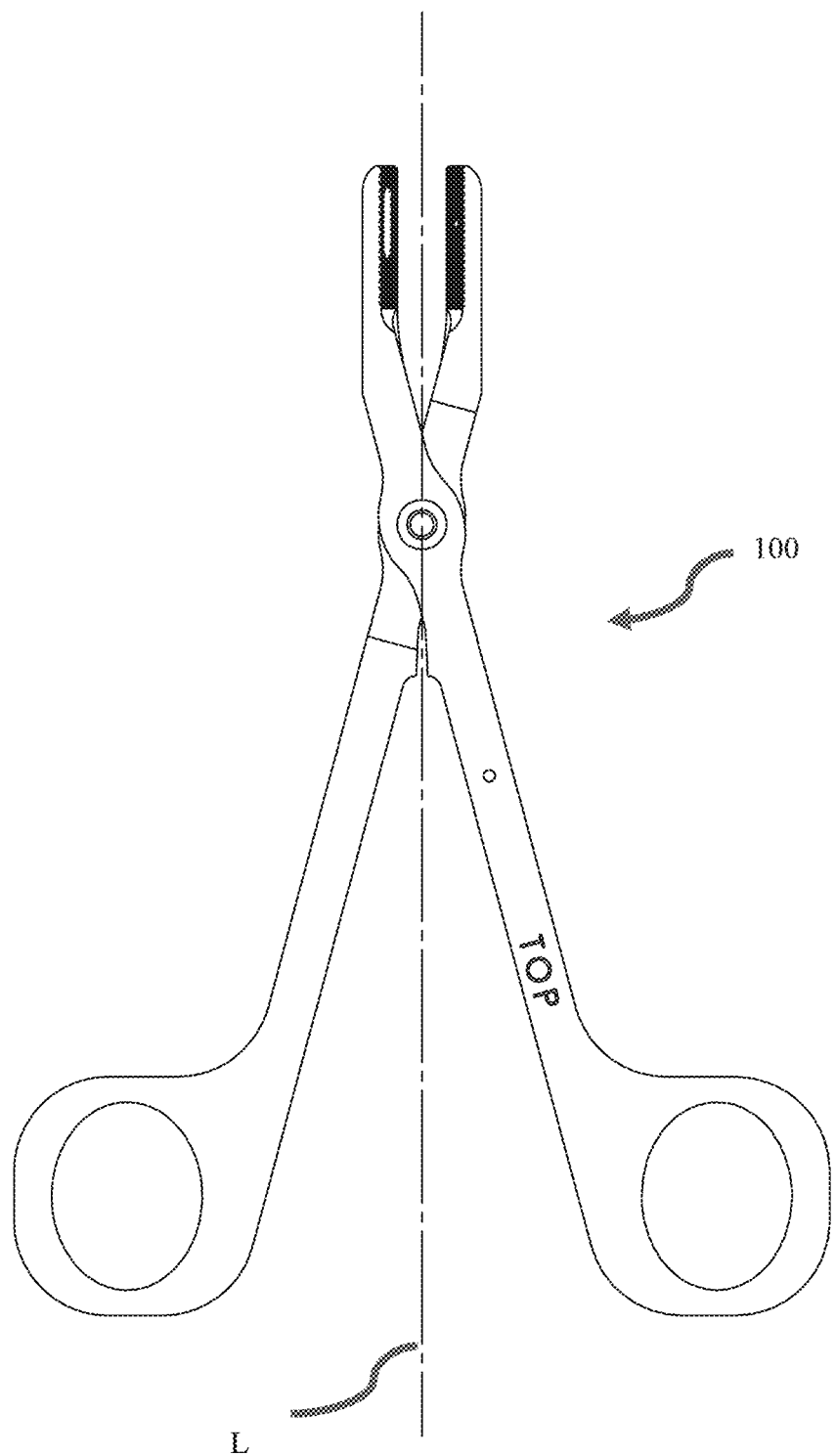

FIG. 1C indicates the central axis of the surgical forceps device as shown in FIG. 1A.

Figure 1D:
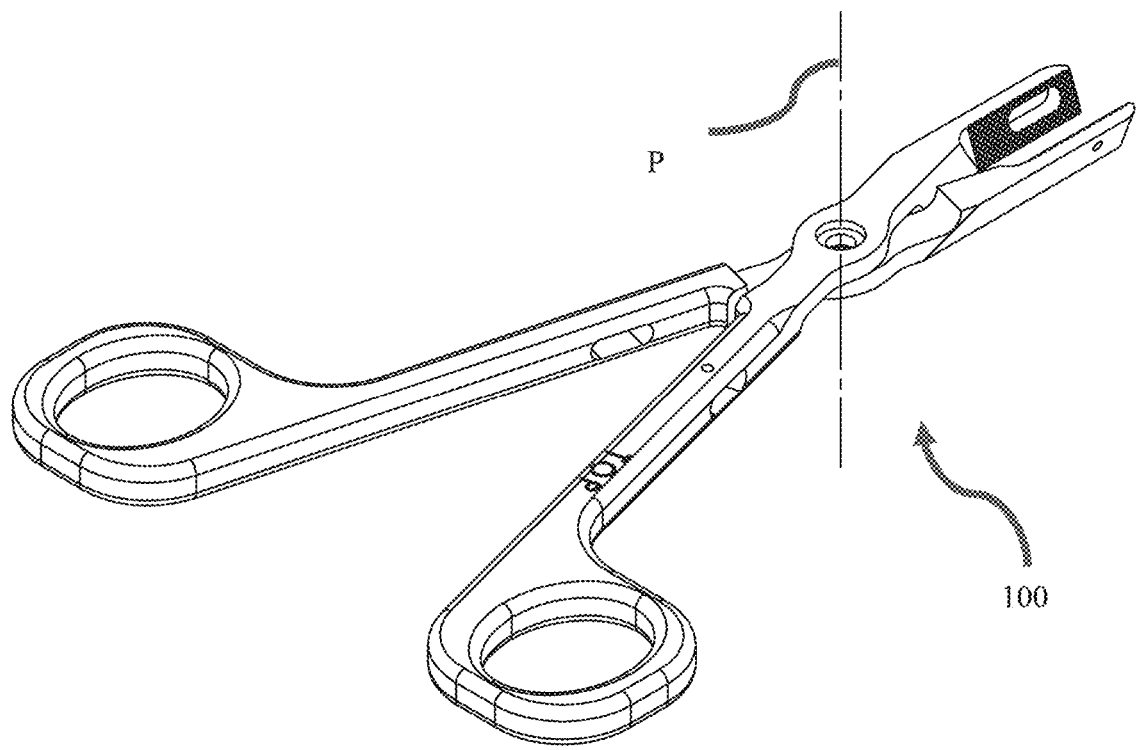

FIG. 1D indicates the axis of the main pivot joint of the surgical forceps device as shown in FIG. 1A.

Figure 2:
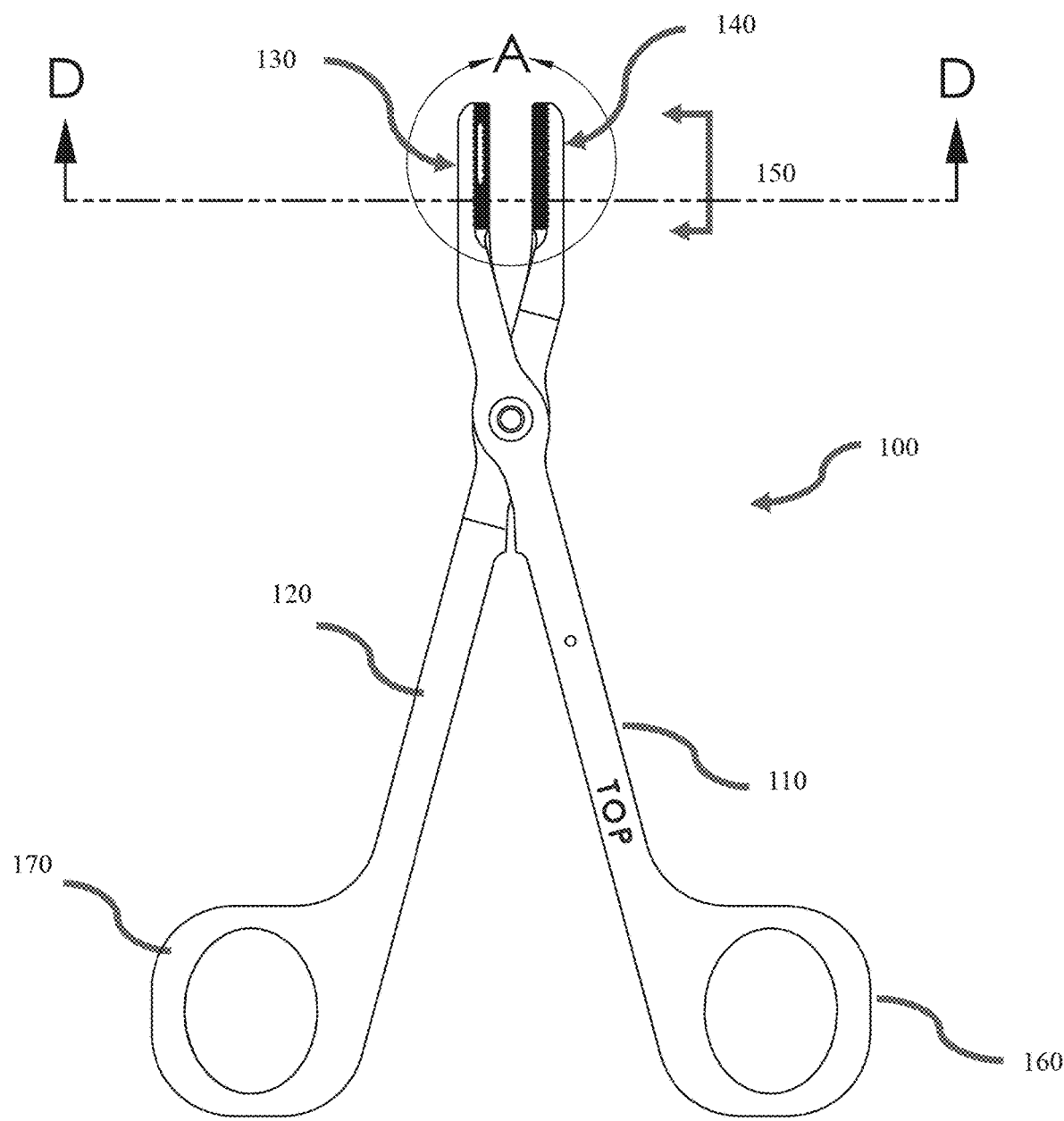

FIG. 2 is a schematic top view diagram of the surgical forceps device illustrating distal and proximal portions according to an exemplary embodiment.

Figure 2A:
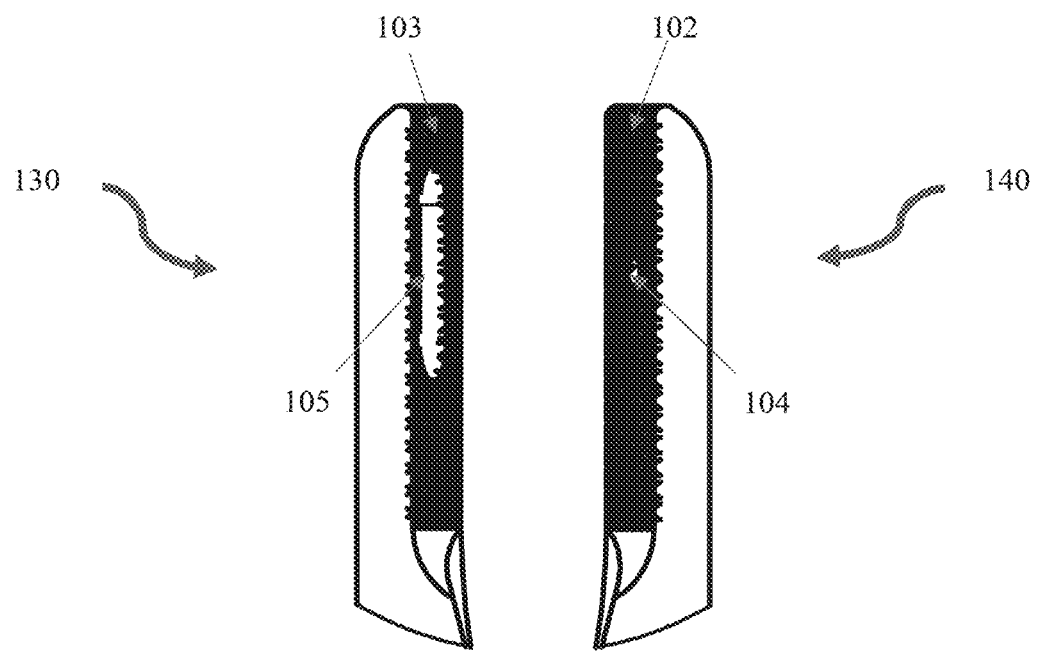

FIG. 2A is a detailed top view of a distal jaw portion of the surgical forceps device as illustrated in FIG. 2 according to an exemplary embodiment.

Figure 2B:
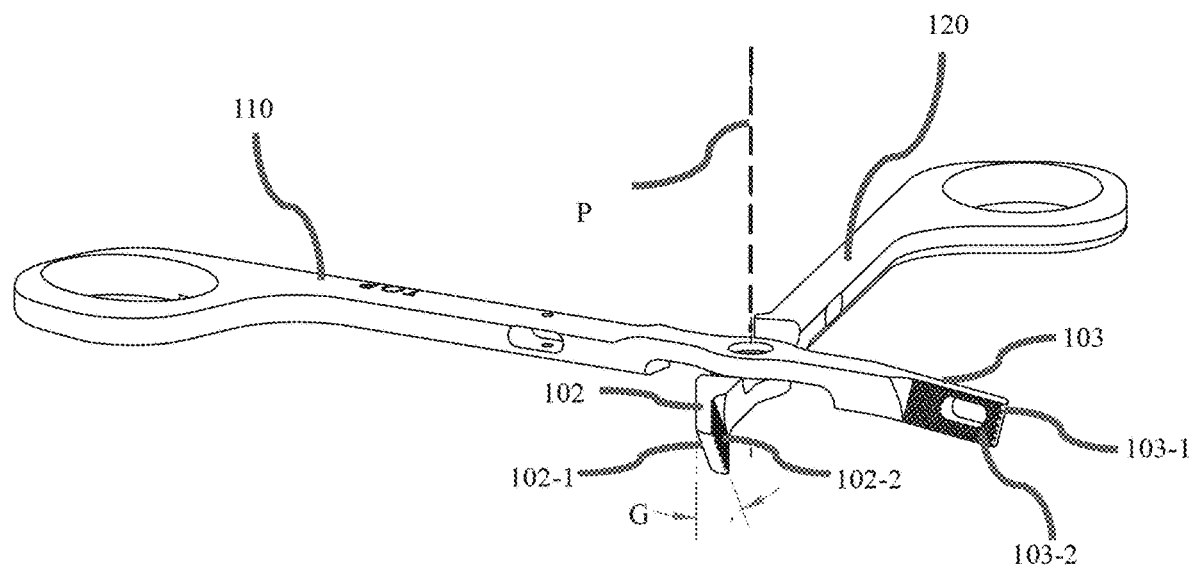

FIG. 2B is a perspective view of the surgical forceps device detailing the distal jaw portion of the surgical forceps device as illustrated in FIG. 2A.

Figure 2C:
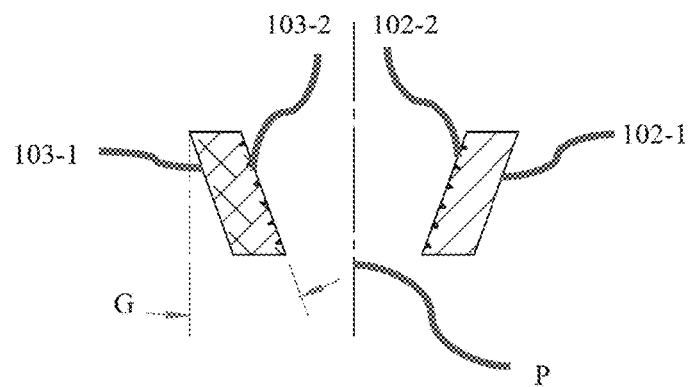

FIG. 2C is a cross-sectional view of the surgical forceps device taken from D-D of FIG. 2, detailing the distal jaw portion of the surgical forceps device.

Figure 3:
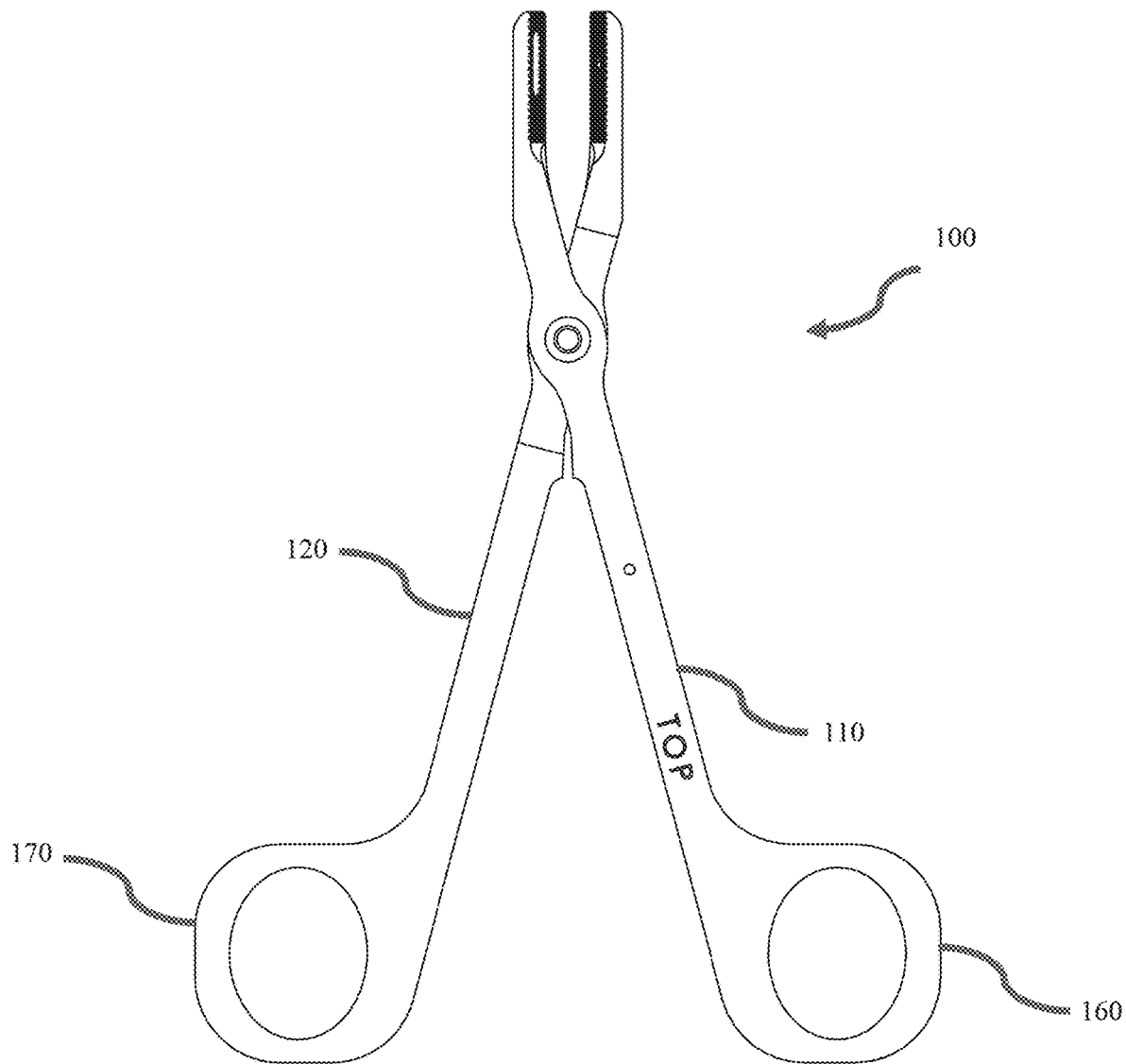

FIG. 3 is a schematic top view diagram of the surgical forceps device illustrating distal and proximal portions according to an exemplary embodiment.

Figure 3A:
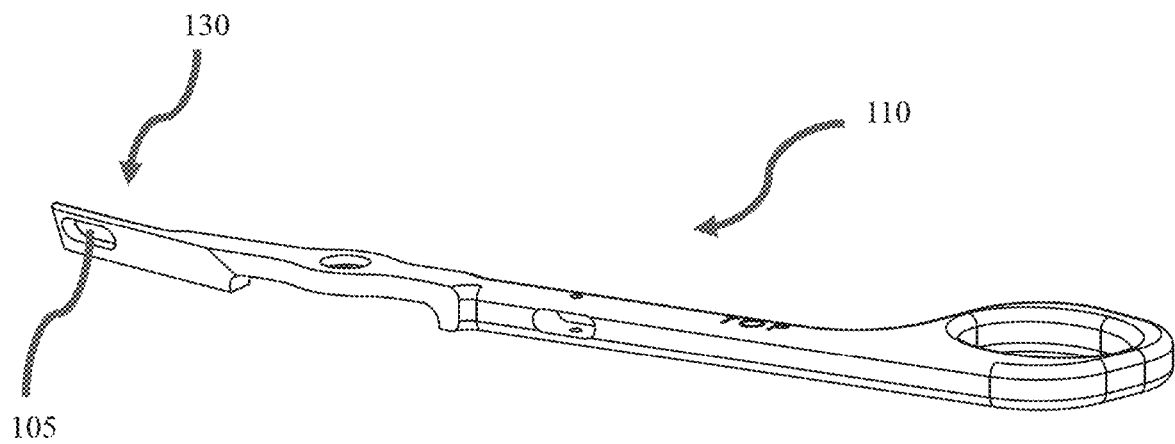

FIG. 3A is a schematic diagram in perspective of a first shank of the surgical forceps device shown in FIG. 3 according to an exemplary embodiment.

Figure 3B:
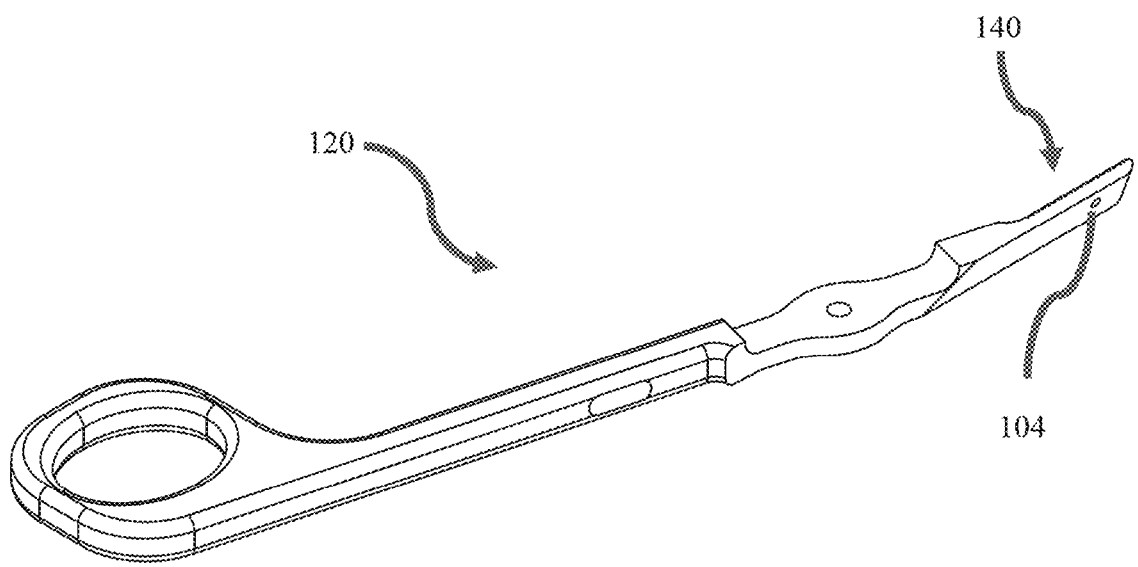

FIG. 3B is a schematic diagram in perspective of a second shank of the surgical forceps device shown in FIG. 3 according to an exemplary embodiment.

Figure 4:
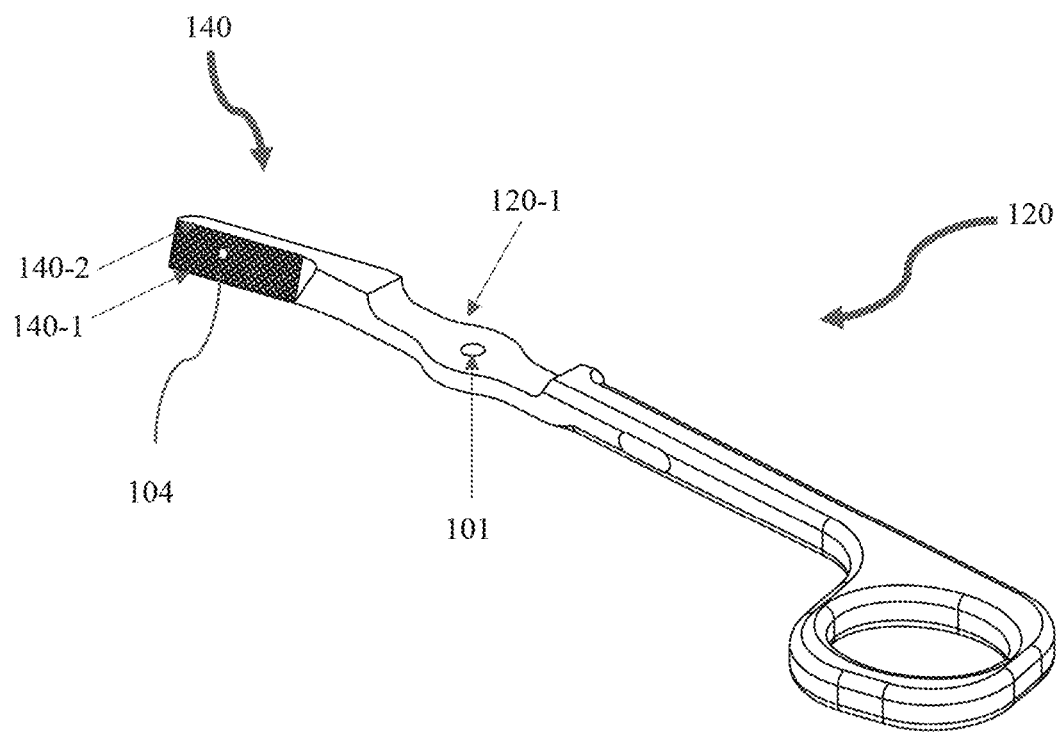

FIG. 4 is a schematic diagram of the second shank of FIG. 3B from an alternative perspective view according to an exemplary embodiment.

Figure 5:
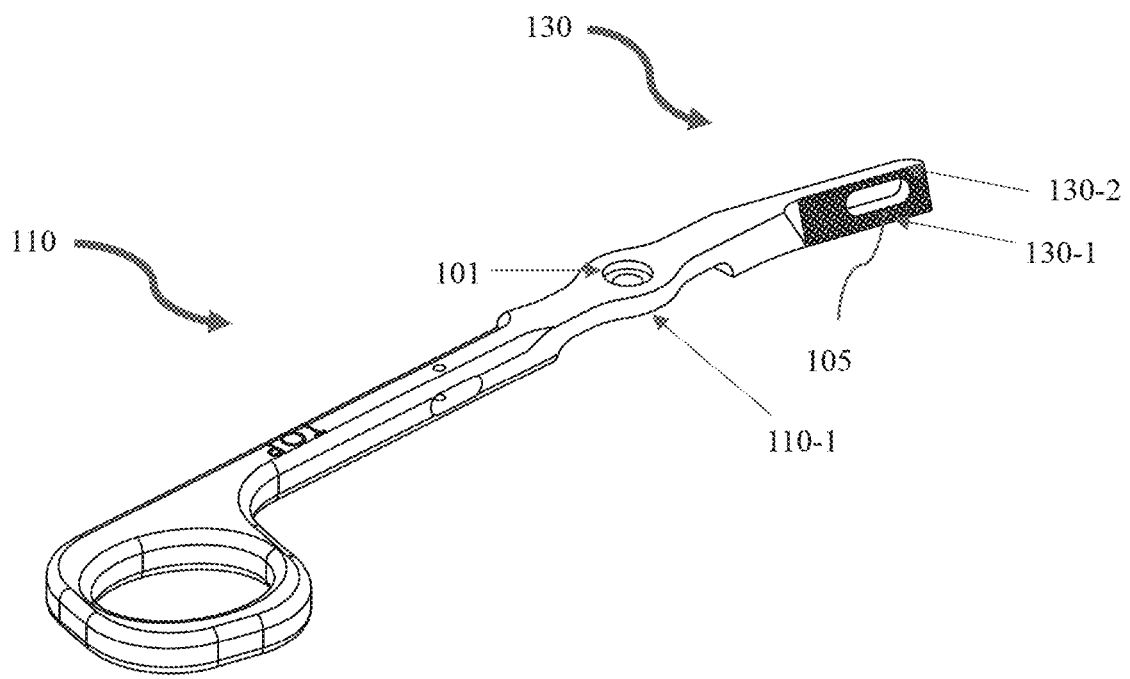

FIG. 5 is a schematic diagram of the first shank of FIG. 3A from an alternative perspective view according to an exemplary embodiment.

Figure 6A:
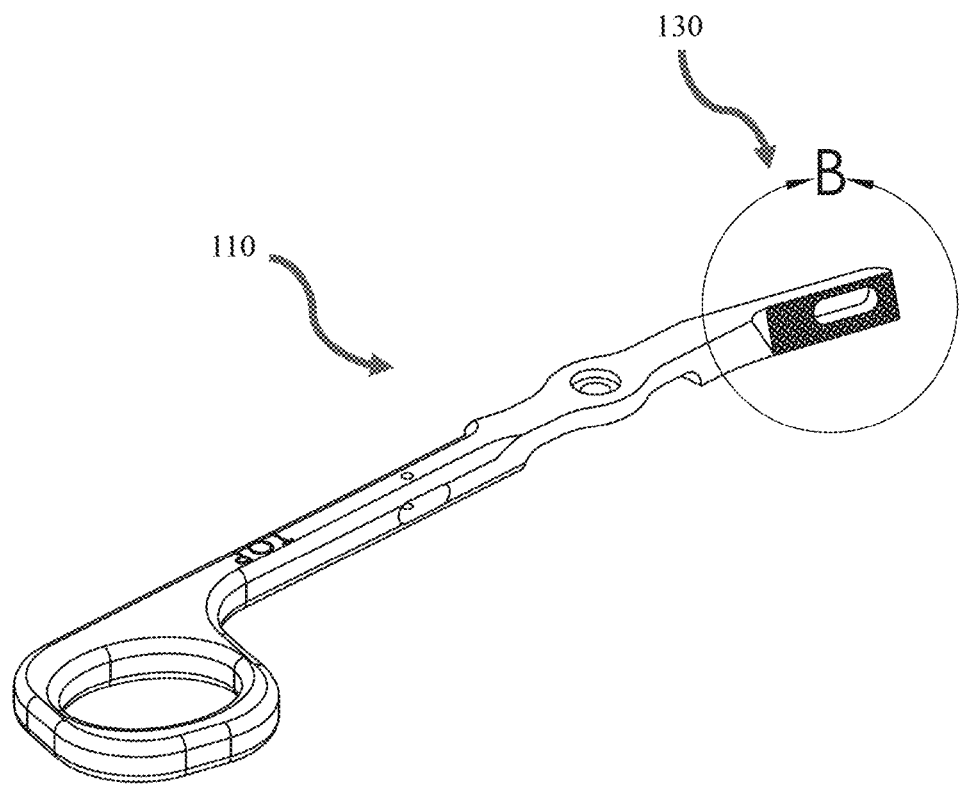

FIG. 6A is a perspective view of the first shank and distal jaw portion of the first shank as illustrated in FIG. 5 according to an exemplary embodiment.

Figure 6B:
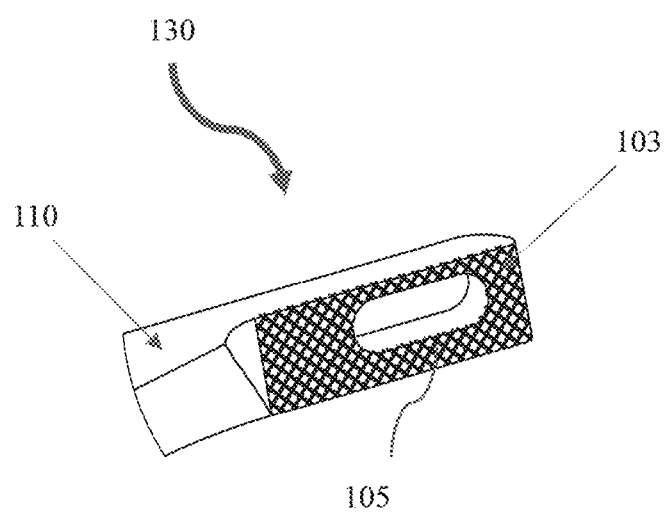

FIG. 6B is a detailed view of the distal portion of the first shank as illustrated in FIG. 6A.

Figure 7A:
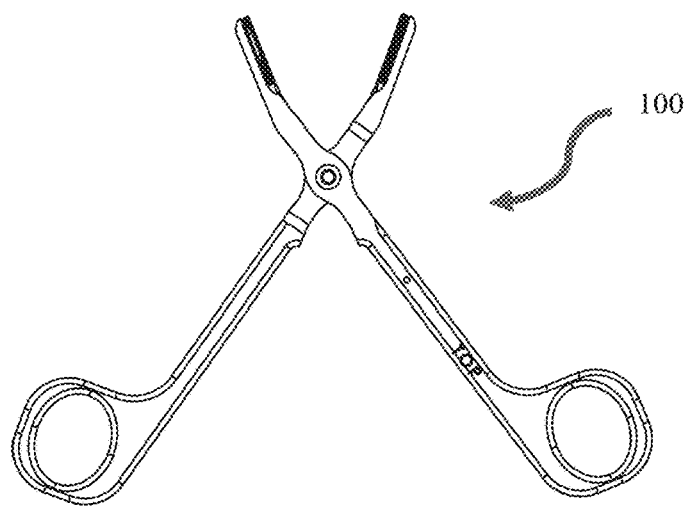
Figure 7B:
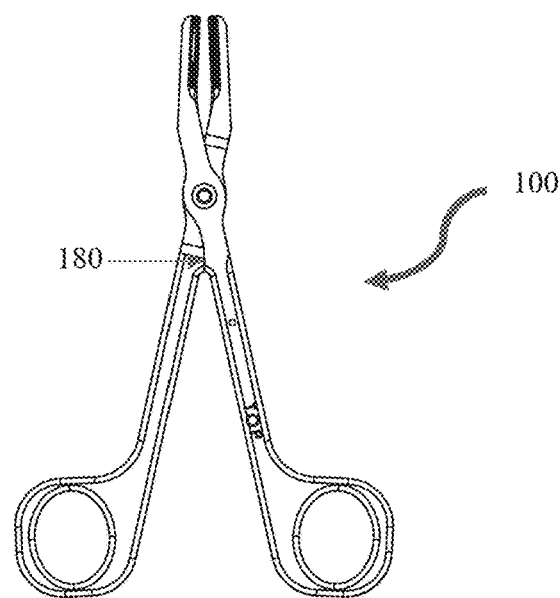
Figure 7C:
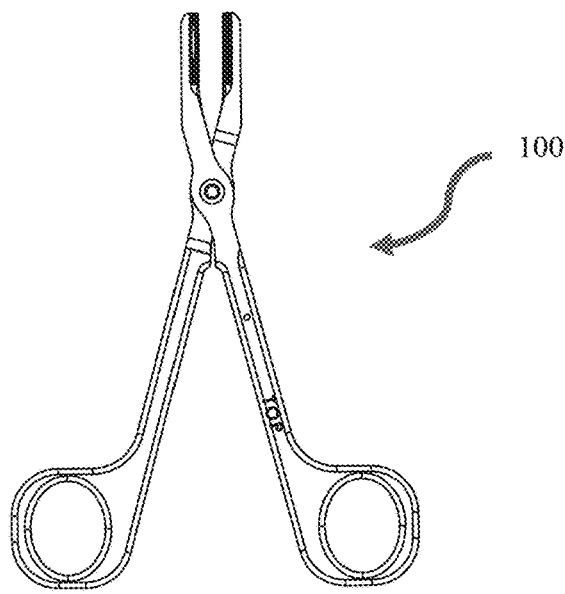

FIGS. 7A-7C are top views of the surgical forceps device according to three different configurations according to an exemplary embodiment.

Figure 8A:
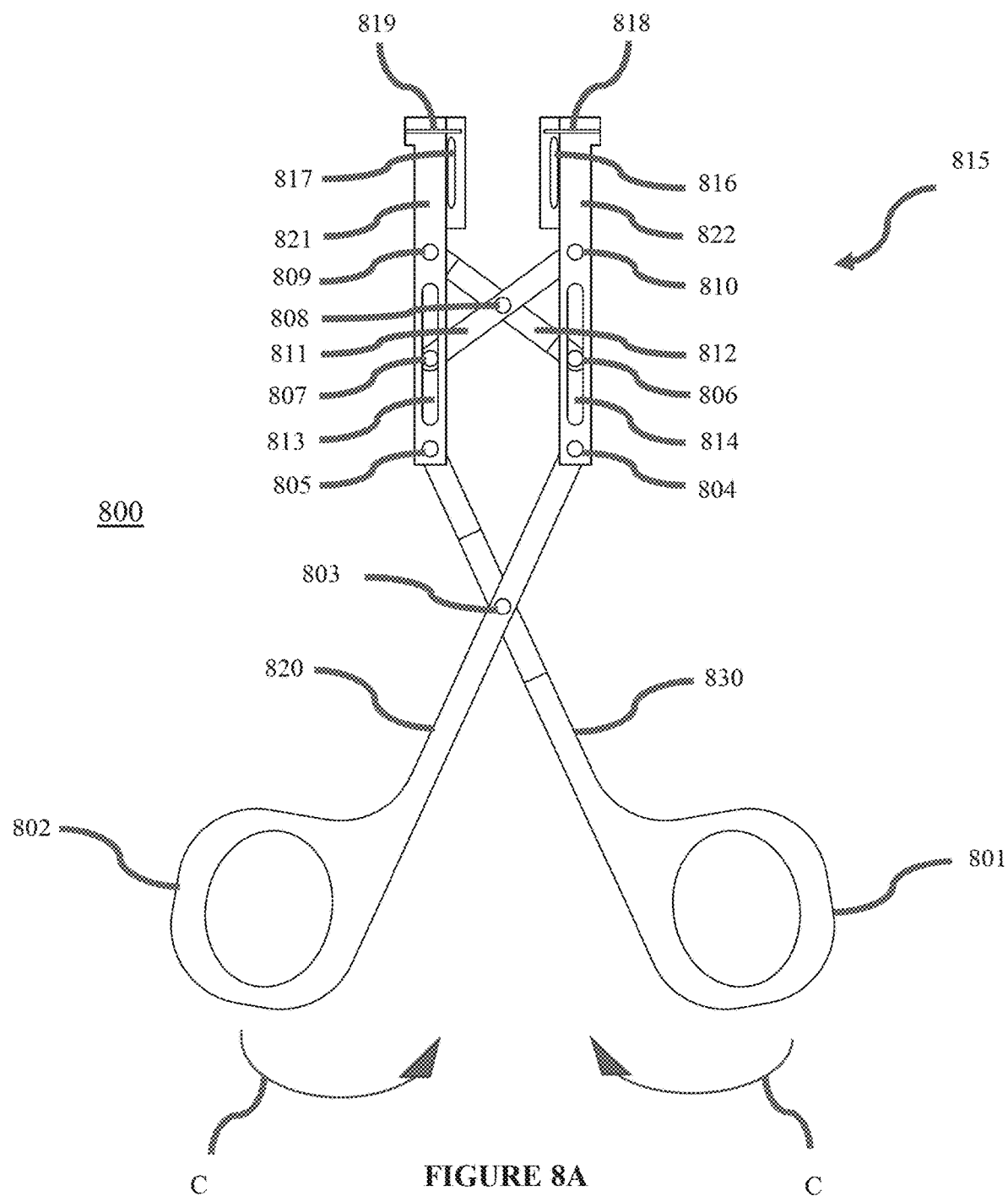

FIG. 8A is a top view of a schematic diagram illustrating a surgical forceps device according to another exemplary embodiment.

Figure 8B:
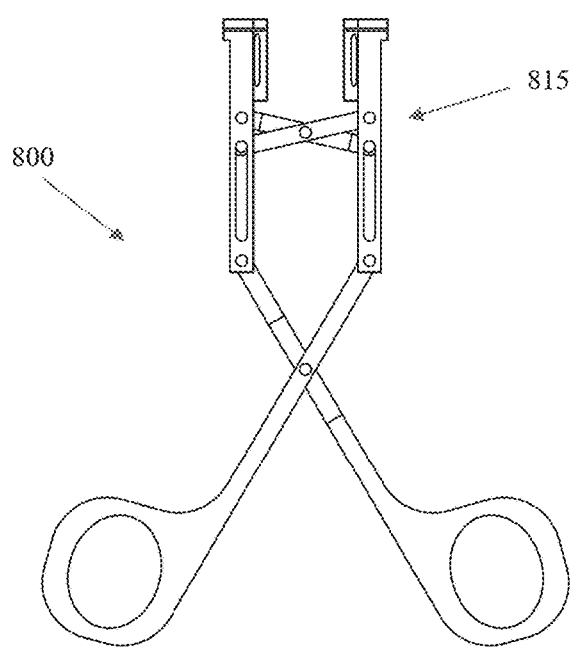
Figure 8C:
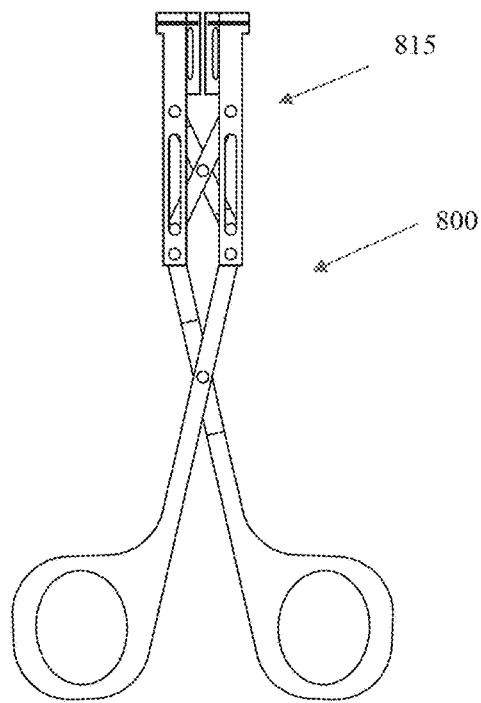

FIGS. 8B-8C are schematic diagrams illustrating biasing configurations of the surgical forceps device illustrated in FIG. 8A according to the exemplary embodiment.

Figure 8D:
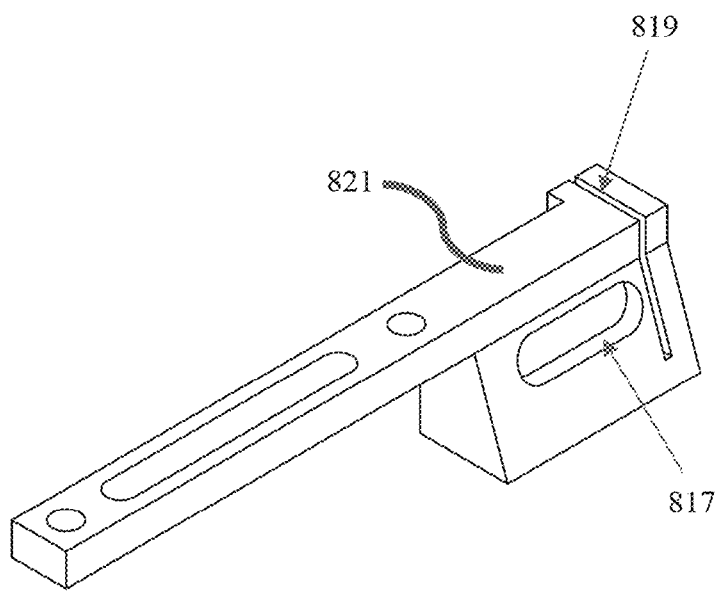

FIG. 8D is a detailed schematic diagram in perspective of a component of the surgical forceps device as illustrated in FIG. 8A.

Figure 9A:
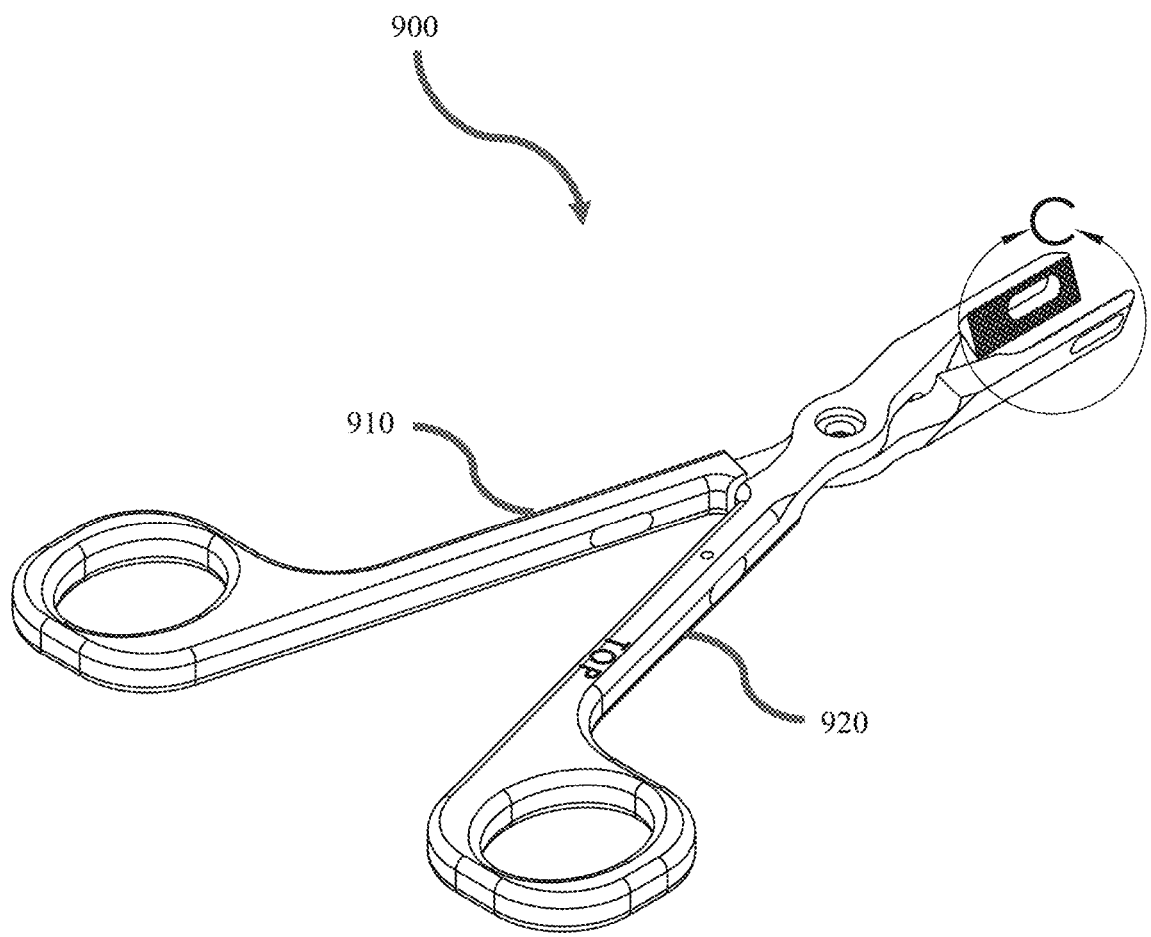

FIG. 9A is a perspective view of a schematic diagram of a surgical forceps device according to a further exemplary embodiment.

Figure 9B:
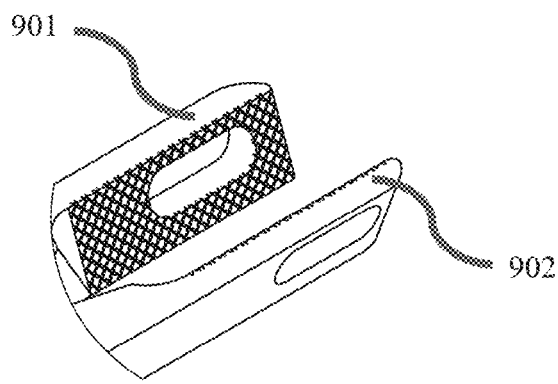

FIG. 9B is a detailed illustration of a distal jaw portion of the surgical forceps device illustrated in FIG. 9A according to an exemplary embodiment.

Figure 10A:
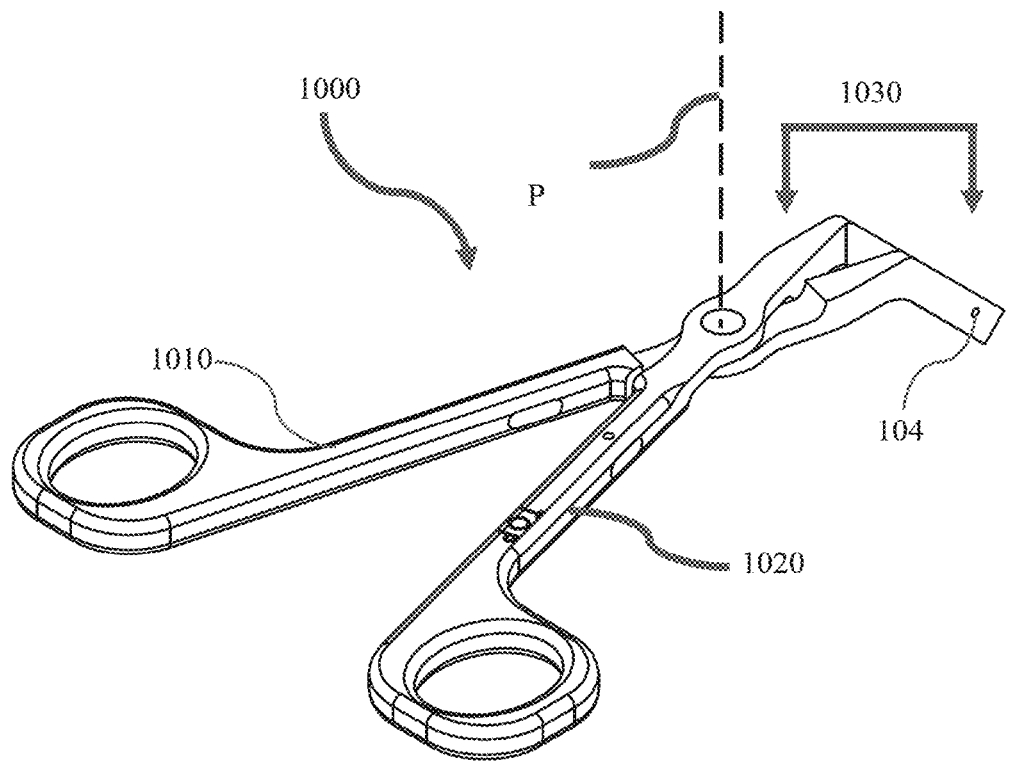

FIG. 10A is a perspective view of a schematic of a surgical forceps device according to another exemplary embodiment.

Figure 10B:
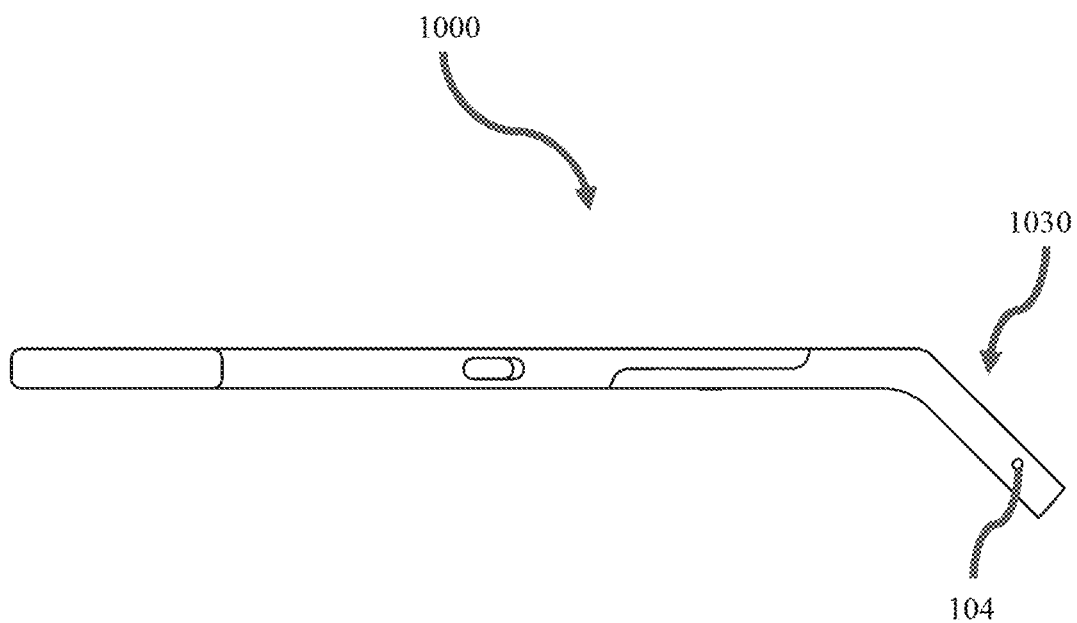

FIG. 10B is a side view of the exemplary embodiment of the surgical forceps device illustrated in FIG. 10A.

Figure 11A:
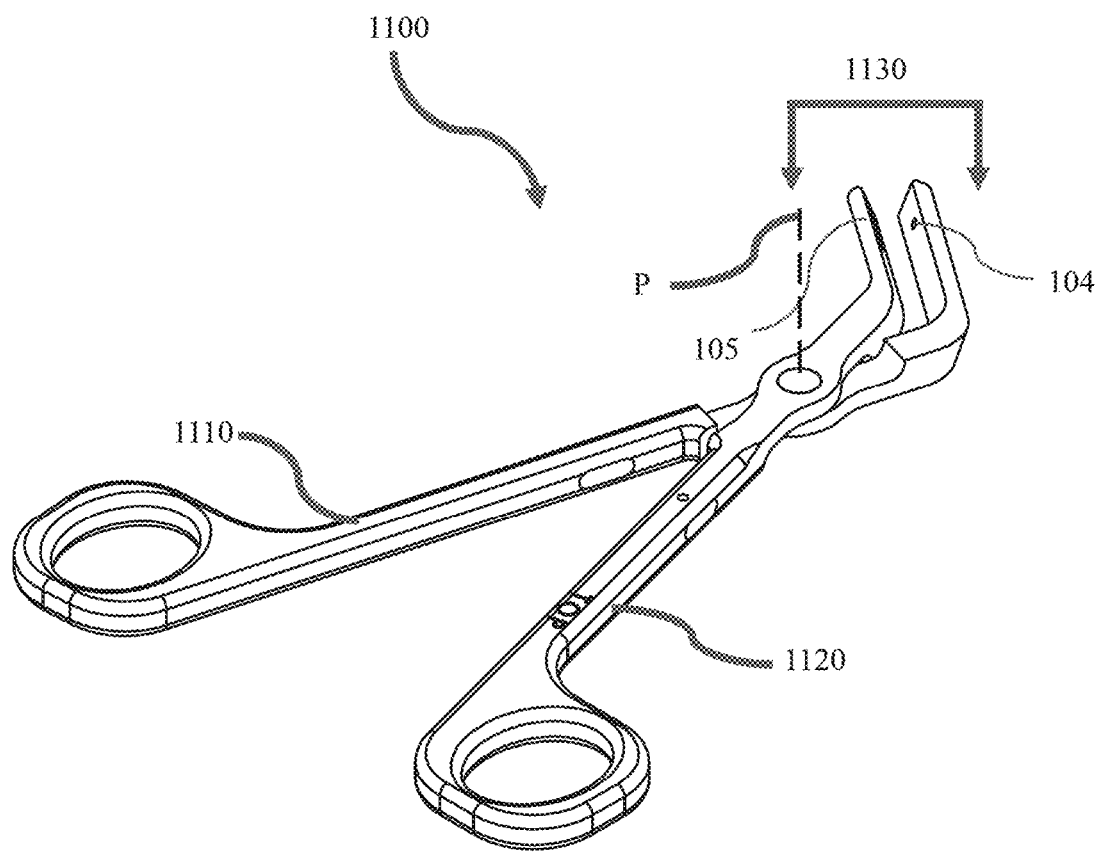

FIG. 11A is a perspective view of a schematic of a surgical forceps device according to another exemplary embodiment.

Figure 11B:
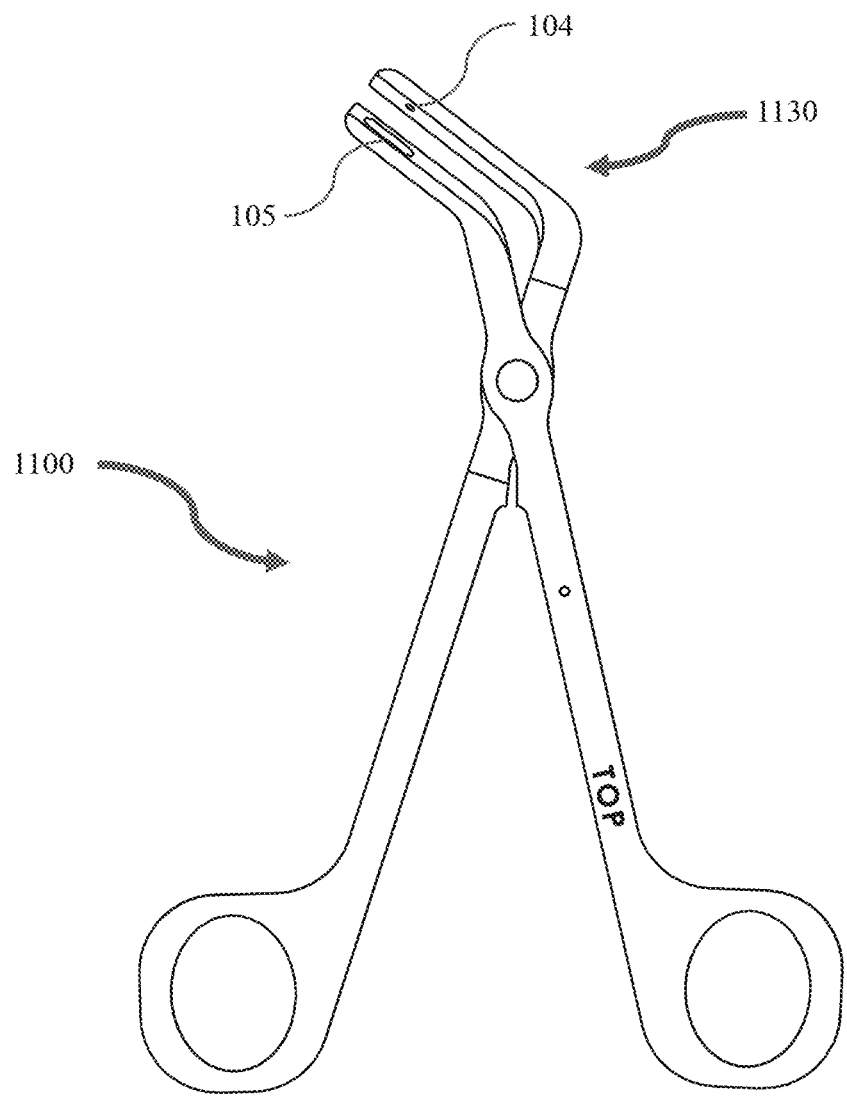

FIG. 11B is a top view of the alternative exemplary embodiment of the surgical forceps device illustrated in FIG. 11A.

Figure 12:
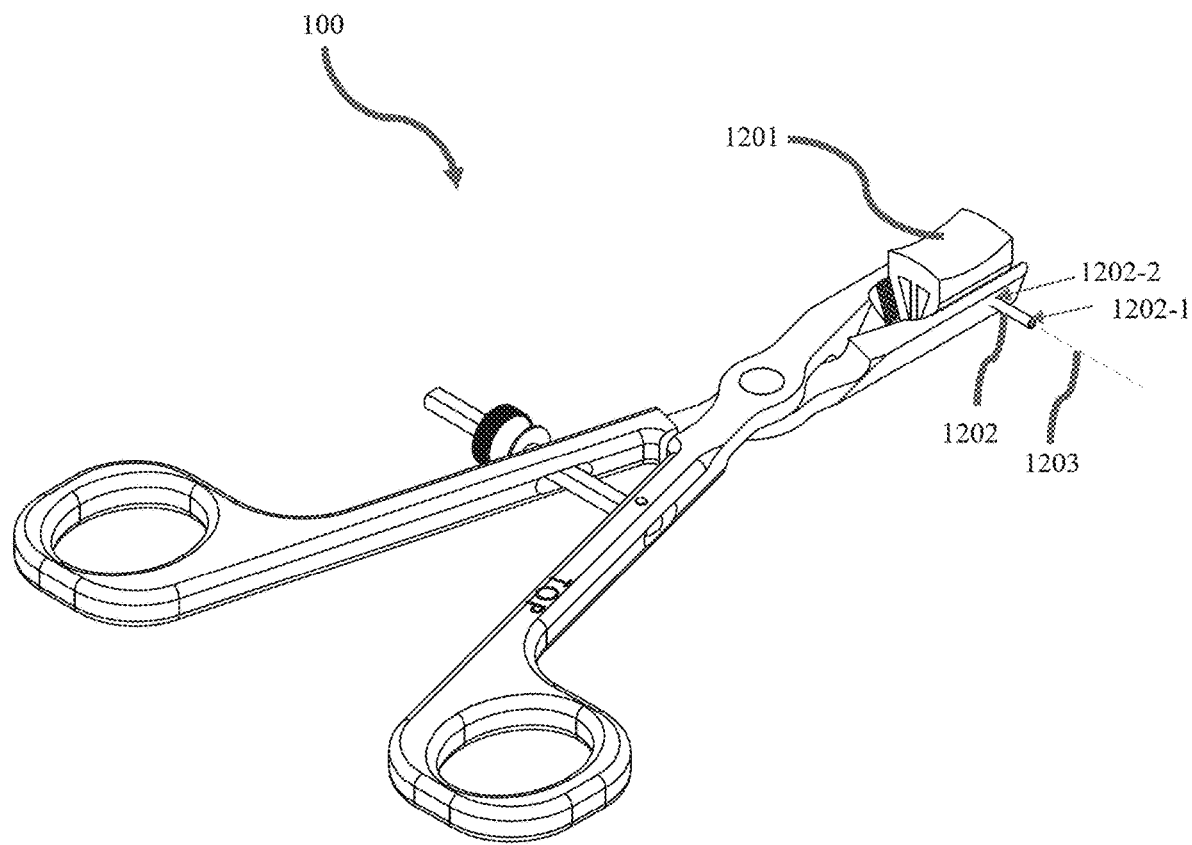

FIG. 12 is a schematic diagram illustrating the method of manipulating the surgical forceps devices disclosed herein to manipulate customized bendable osteochondral allografts during a desired surgical procedure.

DETAILED DESCRIPTION OF THE DISCLOSED SUBJECT MATTER

Various aspects of the novel systems, apparatuses, and methods disclosed herein are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art would appreciate that the scope of the disclosure is intended to cover any aspect of the novel systems, apparatuses, and methods disclosed herein, whether implemented independently of, or combined with, any other aspect of the disclosure. For example, an apparatus may be implemented or a method may be practiced using any number of the aspects set forth herein. In addition, the scope of the disclosure is intended to cover such an apparatus or method that is practiced using other structures, functionality, or structure and functionality in addition to or other than the various aspects of the disclosure set forth herein. It should be understood that any aspect disclosed herein may be implemented by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, and/or objectives. The detailed description and drawings are merely illustrative of the disclosure rather than limiting, the scope of the disclosure being defined by the appended claims and equivalents thereof.

The surgical forceps device and system described herein are useful, for example, in connection with osteochondral allografts that need to be bent about a single axis. An example includes osteochondral allografts that are used in the thumb basal joint (also known as the thumb trapeziometcarpal joint, or thumb carpometacarpal joint), where bending about the radial-ulnar axis increases the convex curvature of the trapezial articular side along the dorsal-volar direction. As the osteochondral allograft is clamped down, the bony struts approximate (come close together). It is understood that the surgical forceps device and system described herein are useful with other bendable allografts. An allograft useful in connection with the apparatuses and devices herein, is described in U.S. Ser. No. 15/125,056, the disclosure of which is incorporated by reference in its entirety herein.

Referring to FIGS. 1A-1D, a surgical forceps device 100 is illustrated according to an exemplary embodiment. The surgical forceps device 100 includes at least a first shank 110, a second shank 120, a first ring hole 160, a second ring hole 170, a hard stop 180, a locking mechanism 190, a distal jaw 150, and a pivoting pin 101. The first and second shanks 110, 120 extend from the first and second ring holes 160, 170 at a proximal portion to a distal jaw 150. The first and second ring holes 160, 170 include apertures therein that are configured to receive a user's fingers. The first and second shanks 110, 120 along with the distal jaw 150 are configured to pivotally move by biasing about pivot axis P (illustrated in FIG. 1D) around the pivot pin 101 as the first and second ring holes 160, 170 are actuated by a user. That is, when the first and second ring holes 160, 170 are pivotally moved (e.g., squeezed) in the direction indicated by arrows C illustrated in FIG. 1B, the first and second shanks 110, 120 move closer to each other at the distal jaw portion 150. The hard stop 180 prevents the first and second shanks 110, 120 from either touching or excessively engaging each other at the distal jaw portion 150. Further, in order to lock the shanks 110, 120 in place, the locking mechanism 190 is engaged by the user. In some embodiments, locking mechanism 190 includes a locking mechanism thumbwheel 190-1 and a locking mechanism screw 190-2 pivotably mounted to first shank 110 and extending through an opening in second shank 120. In use, the user rotates the locking mechanism thumbwheel 190-1 around the locking mechanism screw 190-2 until the thumbwheel 190-1 engages with the second shank 120, thereby preventing the shanks 110, 120 from moving further away from each other. One skilled in the art would appreciate that a segment or portion of the locking mechanism screw 190-2 may be threaded in order to allow engagement with the thumbwheel 190-1. FIGS. 1C-1D indicate the central axis L and the rotation axis P of the main pivot joint of the surgical forceps device 100, respectively. One skilled in the art would appreciate that these axes can be applied to other exemplary embodiments of the surgical forceps device, such as 800, 900, 1000, or 1100 as seen below in FIG. 8A, FIG. 9A, FIG. 10A, and FIG. 11A.

The surgical forceps device 100, which includes the aforementioned features, may be at least partially comprised of materials such as stainless steel, aluminum, or plastic.

Next FIGS. 2A-2B in conjunction with FIG. 2 will be discussed. As noted, FIG. 2, similar to FIGS. 1A-1D is a schematic diagram of the surgical forceps device illustrating the distal and proximal portions according to an exemplary embodiment. The distal jaw 150 will be discussed in further detail with respect to FIGS. 2 and 2A-2B. FIG. 2A is a detailed view of distal jaw 150 taken of surgical forceps device 100 as shown by "A" in FIG. 2. FIG. 2A represents a detailed illustration of the distal jaw 150 including a first distal jaw portion 130 and a second distal jaw portion 140. The first distal jaw portion 130 is associated with the first shank 110, and the second distal jaw portion 140 is associated with the second shank 120. The first distal jaw portion 130 is fixed to the first shank 110, and the second distal jaw portion 140 is fixed to the second shank 120. The first and second distal jaw portions are opposite each other and move in the plane orthogonal to the rotation axis P of the main pivot joint 101 of the surgical forceps device 100. The first distal jaw portion 130 includes the first shank 110, a first clamping jaw 103 and an aperture or opening 105 formed in the first clamping jaw 103. Likewise, the second distal jaw portion 140 includes the second shank 120, a second clamping jaw 102 and an aperture or opening 104 formed in the second clamping jaw 102. As illustrated in FIG. 2A, the first and second clamping jaws 103, 102 and the first and second shanks 110, 120 are opposite to one another as they face each other. As discussed in further detail below the clamping jaws 103, 102 include angled or tapered clamping surfaces.

Further illustration of the surgical forceps device 100 is shown in FIG. 2B and FIG. 2C, which highlight the distal jaw 150 shown in FIG. 2A. FIG. 2B shows a perspective view of surgical forceps device 100 while FIG. 2C shows cross-sectional view D-D as indicated in FIG. 2. As illustrated in FIGS. 2B and 2C, the second clamping jaw 102 includes a polygonal body or shape that includes an outwardly facing angled surface 102-1 and an inwardly facing angled surface 102-2. The inwardly facing angled surface 102-2 and the outwardly facing angled surface 102-1 are inclined at an angle G with respect to the axis P of the main pivot joint 101 as shown by the arrows. In an exemplary embodiment the angle G is at least 19° (nineteen degrees). In another exemplary embodiment, the angle G is at least 20° (twenty degrees) to produce the desired angular position of the clamp surfaces of the bendable osteochondral allograft. However, this is a non-limiting measurement, as one of ordinary skill in the art may achieve variations of this angle (i.e., zero, five, ten, fifteen, twenty, etc. degrees) as desired with either or both of the angled surfaces 102-1 and 102-2.

Similar configuration as set forth above will be appreciated for the first clamping jaw 103. In some embodiments, the first clamping jaw 103 includes an outwardly facing angled surface 103-1 and an inwardly facing angled surface 103-2. The inwardly facing angled surface 103-2 and the outwardly facing angled surface 103-1 are inclined at an angle of at least 200 (twenty degrees) with respect to the axis of the main pivot joint 101. However, as noted above, this is a non-limiting measurement, as one of ordinary skill in the art may achieve variations of this angle (i.e., zero, five, ten, fifteen, twenty, etc. degrees).

One skilled in the art would appreciate that all variations of the surgical forceps device 100 design employ clamping jaws 103, 102 that are set at an angle that produces the final desired angular position of the bendable osteochondral allograft. The specific desired angle is a design parameter that depends on the surgical application. The design of the surgical forceps device 100 could allow for an adjustable angle of the opposing clamping jaws 103, 102.

Next, this paragraph will refer to FIGS. 3A-3B in conjunction with FIG. 3. FIG. 3 is a schematic diagram of the surgical forceps device illustrating distal and proximal portions according to an exemplary embodiment. As illustrated in FIG. 3, and similarly set forth above, the surgical forceps device 100 includes first and second shanks 110, 120. In reference to FIG. 3A, the first shank 110 will be discussed. FIG. 3A illustrates a perspective view of the first shank 110, which includes a first distal jaw portion 130. The first distal jaw portion 130 includes an aperture or a surgical compression screw slot 105 such that a guidewire, screw, or a tube may pass therethrough. Similarly, with respect to the second shank 120, illustrated in FIG. 3B, the second shank 120 includes a second distal jaw portion 140 and a second aperture or the wire guide hole 104 formed in the second clamping jaw 102 such that a guidewire or a tube may pass there through.

One skilled in the art would appreciate that surgical compression screw slot 105 and the wire guide hole 104 serve different purposes. For examples, these apertures 105, 104 may be used for inserting wires, screws, wire guides, drill guides, or other tools needed to secure the allograft in its bent shape. As shown in FIGS. 3A-3B, the wire guide hole 104 on second distal jaw portion 140 accommodates a wire guide while the opposing surgical compression screw slot 105 on first distal jaw portion 130 is large enough for inserting a surgical compression screw. As illustrated in FIGS. 1A and 1B and discussed in further detail below with reference to FIG. 12, the wire guide, e.g., tubular member 1202, may be used to drive a wire guide 1203 across the clamped shanks, emerging through the slot 105 of the opposite clamp face; a hollow compression screw may then be guided along the wire 1203, through the slot 105 of the clamp face 103-2, and threaded into the shanks of the bent allograft.

Additionally, according to some example embodiments, the clamping jaws 102, 103 may include openings or recesses, such as blind, stepped or through holes or slots, to accommodate proud wires, screws, or other anchors that have been used to secure the allograft in its bent shape. These openings or recesses allow the clamping surfaces to remain flush with the allograft. In an exemplary embodiment, a stepped slot may extend along the length of both clamps.

Next FIG. 4 will be discussed. FIG. 4 illustrates a schematic diagram of the second shank 120. The distal jaw portion 140 of the second shank 120 includes the aperture or opening 104 as discussed above. The distal jaw portion 140 of the second shank 120 includes a tapered or angled clamping surface whose long edges 140-1 and 140-2 become parallel with the edges 130-1 and 130-2 of the distal jaw portion 130 of the first shank 110 upon clamping the bendable allograft into its final configuration. A recess 120-1 formed in the second shank 120 is illustrated. The recess 120-1 in the second shank 120 is configured to receive or mate with the first shank 110 such that the first shank 110 and the second shank 120 engage with each other and form a pivoting connection as they are held together at a pivoting pin joint 101.

Similarly, FIG. 5 illustrates a schematic diagram of the first shank. The distal jaw portion 130 of the first shank 110 includes the aperture or the surgical compression screw slot 105 as discussed above. The surgical compression screw slot 105 is formed in the first shank 110, wherein the distal jaw portion 130 of the first shank 110 includes a tapered or angled clamping surface whose long edges 130-1 and 130-2 become parallel with the edges 140-1 and 140-2 of the distal jaw portion 140 of the second shank 120 upon clamping the bendable allograft into its final configuration. A recess 110-1 formed in the first shank 110 is illustrated. The recess 110-1 in the first shank 110 is configured to receive or mate with the second shank 120 such that the first shank 110 and the second shank 120 engage with each other and form a pivoting connection as they are held together at a pivoting pin joint 101.

Next referring to FIGS. 6A-B, perspective views of the first shank 110 and distal jaw portion 130 of the first shank 110 are illustrated. In particular, detail view "B" outlined in FIG. 6A is taken at the distal jaw portion 130 of the first shank 110. The detail view "B" is further illustrated in FIG. 6B. As noted in FIG. 6B, distal jaw portion 130 of the first shank 110 includes an aperture or a surgical compression screw slot 105, and the tapered or angled surface of the clamping jaw 103 of the first shank 110 includes a textured surface including a serrated or knurled surface. Having a textured surface that includes a serrated or knurled surface allows for further grasping and secure engagement of the customized bendable osteochondral allograft as it is being manipulated and maneuvered during a surgical procedure. One skilled in the art would appreciate that such configuration of the textured surface is not limited to the first shank 110, as such configuration may also be applicable to the second shank 120. In some exemplary embodiments, the clamping jaws 103, 102 of the surgical forceps device 100 may be entirely or partially serrated or knurled to minimize slippage of the allograft in the clamping jaws 103, 102.

Next referring to FIGS. 7A-7C, top views of the surgical forceps device 100 according to three different configurations are illustrated. As noted, FIG. 7A illustrates the surgical forceps device 100 in an extended or open configuration wherein the first and second shanks 110, 120 are separated from each other. FIG. 7B illustrates a closed configuration wherein the first and second shanks 110, 120 bias towards each other and the distal jaw portion 150 indicates that clamping jaws 103, 102 of the respective shanks are nearly abutting each other. In this closed position, a hard stop 180 prevents the clamping jaws 103, 102 from either touching or excessively engaging each other. Lastly, FIG. 7C illustrates an intermediate position that is between the open position illustrated in FIG. 7A and the closed position illustrated in FIG. 7B. The intermediate position illustrated in FIG. 7C represents a position where the surgical forceps device 100 is configured to engage, hold and maintain the position of a bent osteochondral allograft. One skilled in the art would appreciate that the surgical forceps device 100 consists of two parts pivoted at a single joint in a scissor-like design, such that the clamping jaws 103, 102 become parallel, or nearly parallel, to each other when the osteochondral allograft has been bent by the desired amount.

Next, referring to FIGS. 8A-8D a surgical forceps device according to another exemplary embodiment is illustrated.

The surgical forceps device illustrated in FIG. 8A is similar to the surgical forceps device illustrated in FIGS. 1A-1D, for example, as it also includes first and second ring holes 801, 802 and pair of shanks 830, 820, which are similar to the first and second ring holes 160, 170, and the pair of shanks 110, 120, respectively, discussed above. Additionally, the surgical forceps device of FIG. 8A includes a pivot pin 803, similar to pivot pin 101 illustrated in FIG. 1B, for example, that mates and holds together in place the pair of shanks 830, 820. The first and second shanks 830, 820 are configured to pivotally move by biasing around the pivot pin 803 as the first and second ring holes 801, 802 are actuated by a user. That is, when the first and second ring holes 801, 802 are pivotally moved (e.g., squeezed) in the direction indicated by arrows illustrated in FIG. 8A, the first and second shanks 830, 820 move closer to each other at a distal jaw portion 815.

Some of the differences of the surgical forceps device 800 include the pair of shanks 830, 820 and the distal jaw 815, which are structurally and functionally different than the pair of shanks 110, 120 and the distal jaw portion 150 of the surgical forceps device 100 illustrated in FIGS. 1A-1D, for example. The pair of shanks 830, 820, as illustrated in FIG. 8A, extend from the pair of first and second ring holes 801, 802 to first and second joints 804, 805 in a non-parallel fashion to a central axis of the surgical forceps device 800. That is, the pair of shanks 830, 820 rotate in the plane orthogonal to the axis P of the main pivot joint 803 of the surgical forceps device 800. Further, the pair of clamping jaw portions 822, 821 are pivotally connected to shanks 820, 830 and extend from the first and second joints 804, 805 to a distal-most end of the surgical forceps device 800. This portion of extension of the surgical forceps device 800 is parallel to the central axis of the surgical forceps device 800.

Now, the distal jaw 815 of the surgical forceps device 800 will be discussed in further detail. The distal jaw 815 is different in configuration, functionality and structure from the distal jaw 150 of the surgical forceps device 100. The distal jaw 815 is a positioning or a multi-jointed mechanism that ensures that clamping jaw portions 821, 822 remain parallel to each other at all positions as the first and second ring holes 801, 802 bias towards each other as shown by the arrows C in FIG. 8A. The jaw portions 821, 822 may include a polygonal body aligned parallel to the central axis of the surgical forceps 800, the polygonal body of each respective clamping jaw having an outwardly facing surface substantially planar to the associated shank and an inwardly facing tapered surface.

The positioning mechanism of the surgical forceps device 800 includes a pair of sliding joints 806, 807, a pivoting joint 808, a pair of fixed joints 809, 810, a pair of links 811, 812, and a pair of slots 813, 814.

The pair of links 811, 812 are connected in a cross-configuration as first link 811 is positioned over second link 812 at the pivoting joint 808. The pivoting joint 808 is aligned along the central axis of the surgical forceps device 800. On one end, the pair of links 811, 812 are affixed to the respective pair of clamping jaw portions 822, 821 at the respective pair of fixed joints 810, 809, and on the other opposing end the pair of links 811, 812 are affixed to the respective pair of sliding joints 807, 806. The fixed joints 809, 810 are pivoting joints formed in the respective pair of clamping jaw portions 821, 822. That is, first fixed joint 809 is a pivoting or a linkage joint formed in the first clamping jaw portion 821 that allows the second link 812 to rotate around the fixed joint 809 while the pivoting joint 808 translates along the central axis L of the surgical forceps device 800. Similarly, the second fixed joint 810 is a pivoting or a linkage joint formed in the second clamping jaw portion 822 that allows the first link 811 to rotate around the fixed joint 810 while the pivoting joint 808 translates along the central axis of the surgical forceps device 800.

Still referring to FIG. 8A, the pair of links 811, 812 are affixed to the respective pair of sliding joints 807, 806 on the opposing end. The sliding joints 807, 806 are configured to translate in respective slots 813, 814 between a first position and a second position as shown in FIGS. 8B and 8C. The sliding joints 807, 806 may be similar to the fixed joints 809, 810 in that they act similarly to a pivoting or a linkage joint, but they are also configured to translate between different positions in their respective slots 813, 814. The first sliding joint 807 is positioned in the slot 813 that is formed in the first clamping jaw portion 821. The second sliding joint 806 is positioned in the slot 814 that is formed in the second clamping jaw portion 822. The length of the slots 813, 814 may correspond to the distance travelled between the two clamping jaws portions 821, 822 as they come close to each other upon actuation of the first and second ring holes 801, 802 (as shown by the arrows C in FIG. 8A).

As the first and second ring holes 801, 802 are actuated from an open position shown in FIG. 8B to an intermediate or a closed position shown in FIG. 8C, the sliding joints 806, 807 translate from a distal end of their respective slots 814, 813 to a proximal end of their respective slots 814, 813. During this sliding transition, the pair of links 811, 812 go from a compressed configuration to an expanded or extended configuration. As the links 811, 812 transition to an expanded or extended configuration and the sliding joints 806, 807 translate to the proximal end of their respective slots 814, 813, the clamping jaw portions 822, 821 move closer to each other while maintaining parallel orientation between the two heads. Additionally, the pivoting joint 808 continues to maintain its alignment with the central axis of the surgical forceps device 800. As noted above, the clamping jaws portions 821, 822 maintain their parallel orientation with respect to each other in order to ensure the osteochondral allograft that has been bent by the desired amount continues to be securely positioned in place between the clamping jaw portions 821, 822 as it is being manipulated during a surgical procedure.

Still referring to FIG. 8A, the distal jaw 815 further includes recess 819 formed in clamping jaw portion 821. The recess 819 may be a guiding slot that accommodates a saw blade. Shown in further detail in FIG. 8D is a detailed illustration of the distal clamping jaw portion 821. As noted in FIG. 8D, in conjunction with FIG. 8A, the recess 819 may run parallel to the face of the distal end of the clamping jaw portion 821 such that it extends the width of the clamping jaw portion and extends down from the top face. Although discussion herein is made with respect to recess 819 formed in clamping jaw portion 821, one skilled in the art would appreciate that similar configuration applies to recess 818 formed in clamping jaw portion 822. The pair of recesses 819, 818 formed in the respective clamping jaw portions 821, 822 are in line with each other.

As shown in FIG. 8D, the clamping jaw portion 821 includes recess 819 and opening 817. The opening 817 may be similar to openings 104, 105 discussed above with respect to surgical forceps device 100. The opening 817, as illustrated, may be a screw slot that is longitudinal, running partially along a length of the distal end of the clamping jaw portion 821, and which is configured to receive at least one screw therein. The opposing clamping jaw portion 822 may also include a recess 818 and a similar opening or slot 816.

Alternatively, the opposing clamping jaw portion 822 may only include the recess 818 and not the opening or slot 816.

Next, referring to FIGS. 9A-9B, surgical forceps device 900 according to another alternative exemplary embodiment is disclosed. The surgical forceps device 900 is generally similar to the surgical forceps device 100 illustrated in FIGS. 1A-D; however, it includes a variation of clamping jaws 901, 902 at the distal jaw portion. As shown in further detail in FIG. 9B, which is a detail view of FIG. 9A taken at "C," the clamping jaws 901, 902 include tapered or angled clamping surfaces that are offset from the central axis of the surgical forceps device 900. Additionally, the clamping jaws 901, 902 include similar opening configuration as opening 817 discussed in FIG. 8D, wherein the opening may be a screw slot that is longitudinal, running partially along a length of the distal end of the clamping jaw 821, and which is configured to receive at least one screw therein. As illustrated in FIG. 9B, such openings are formed on both clamping jaws 901, 902.

Next, referring to FIGS. 10A-10B, surgical forceps device 1000 according to another alternative exemplary embodiment is disclosed. The surgical forceps device 1000 is generally similar to the surgical forceps device 100 illustrated in FIGS. 1A-D; however, it includes a variation of the distal jaw portion 1030. The distal jaw portion 1030 has been bent out of the plane orthogonal to the rotation axis P of the main pivot joint. An isometric view of 1000 is shown in FIG. 10A and a side view indicating the clear bend of the distal jaw portion is shown in FIG. 10B. The function of surgical forceps 1000 is similar to the function of surgical forceps 100 and the clamping jaws of the distal jaw portion 1030 allow a bendable osteochondral allograft to be bent and manipulated, but the bend at the distal jaw portion 1030 may be beneficial in certain surgical applications. One skilled in the art may appreciate that the angle of the bend may vary and would be dependent on surgical application.

FIG. 11A-B will now be discussed. FIG. 11A illustrates an isometric view of another alternative exemplary embodiment of a surgical forceps device 1100. Similar to surgical forceps device 1000, the distal jaw portion 1130 of surgical forceps device 1100 has a bend. The bend of the distal jaw portion 1130 is different than distal jaw portion 1030 in that the bend lies in the plane orthogonal to the rotation axis P of the main pivot joint as can be seen in the top view illustration shown in FIG. 11B. One skilled in the art may appreciate that the angle of the bend may vary depending on surgical application. One skilled in the art may also appreciate that the bending of the distal jaw portions 1030 and 1130 indicate two possible angles and bending planes, but are not limiting.

Next, FIG. 12 will be discussed, which is a schematic diagram illustrating the method of manipulating the surgical forceps devices disclosed herein to manipulate customized bendable osteochondral allografts during a desired surgical procedure. As shown in FIG. 12, surgical forceps device 100 is shown as if engaged by a user at the first and second ring holes 160, 170, which bias the first and second shanks 110, 120. Although the surgical forceps device 100 is shown and discussed herein, one skilled in the art would appreciate that other exemplary embodiments disclosed herein such as in FIGS. 8A-8D, 9A-9B, 10A-10B, and 11A-11B may alternatively be used to perform the steps discussed herein. As shown, FIG. 12 includes the osteochondral allograft 1201 that is positioned between the clamping jaws 102, 103.

Further, FIG. 12 illustrates a tubular member 1202 that is affixed or engaged with the distal jaw portion 150 of the surgical forceps device 100. In particular, the tubular member 1202 engages or mates with the wire guide hole 104 discussed above with respect to FIG. 3B. The tubular member 1202 may be a separate or independent piece such that the tubular member 1202 and the surgical forceps device 100 are sold as part of a kit or package. Alternatively, the tubular member 1202 may be manufactured with the surgical forceps device 100 such that the two components comport to be a single piece. The tubular member 1202 includes first and second opposing ends 1202-1, 1202-2 and a lumen extending there through between the first and second ends 1202-1, 1202-2. The second end 1202-2 of the tubular member 1202 includes an outer diameter configured to be received within the opening 104 in the shank 120. As shown in FIG. 12, the tubular member 1202 mates or engages with shank 120 as it securely positions itself in the opening 104 in the shank 120 and extends away from the shank 120. In other words, the axis of the tubular member 1202 is orthogonal to the central axis L of the surgical forceps device 100 when the clamping jaws 130 and 140 are in the parallel position with the bendable osteochondral allograft is in its final configuration as seen in FIG. 7C and in FIG. 12. As such, by engaging the tubular member 1202 with the opening 104, a throughway passage is created that extends from first end 1202-1 to the opposing side or face of shank 120.

Still referring to FIG. 12, a guidewire 1203 is introduced through the lumen of the tubular member 1202 such that the guidewire 1203 extends from the first end 1202-1 to the second end 1202-2 of the tubular member 1202 and past the wire guide hole 104 formed in the shank 120. Further, a screw gun or a similar tool may be employed or used by a user that engages with the guidewire 1203 in order to rotate the guidewire 1203 along its own axis that aids in engaging the guide wire 1203 with the allograft 1201 positioned between the clamping jaws 102, 103. Similar to the introduction of the guidewire 1203 via the tubular member 1202 and guide wire hole 104, a surgical screw may be introduced into the allograft 1201 via the surgical compression screw hole 105 formed in shank 110.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations can be understood and effected by those skilled in the art in practicing the claimed disclosure, from a study of the drawings, the disclosure and the appended claims.

It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open-ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "such as" should be interpreted as "such as, without limitation;" the term 'includes" should be interpreted as "includes but is not limited to"; the term "example" is used to provide exemplary instances of the item in discussion, not an exhaustive or limiting list thereof, and should be interpreted as "example, but without limitation"; adjectives such as "known," "normal," "standard," and terms of similar meaning should not be construed as limiting the item described to a given time period or to an item available as of a given time, but instead should be read to encompass known, normal, or standard technologies that can be available or known now or at any time in the future; and use of terms like "preferably," "preferred," "desired," or "desirable," and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, that the result is within 80% of the value, within 90% of the value, within 95% of the value, or within 99% of the value. Also, as used herein "defined" or "determined" can include "predefined" or "predetermined" and/or otherwise determined values, conditions, thresholds, measurements, and the like.

We claim:

1. A surgical clamp system, comprising:
    a forceps device comprising first and second shanks, each shank comprising a distal jaw portion having an inwardly facing surface and an outwardly facing surface, the first and second shanks configured to pivot about a pivot axis between open and closed configurations, wherein the distal jaw portions are disposed in adjacent relationship in the closed configuration, the jaw portion of the second shank defining an opening therethrough from said inwardly facing surface to said outwardly facing surface,
    wherein the respective inwardly facing surface associated with the jaw portion of the first shank opposes the respective inwardly facing surface associated with the jaw portion of the second shank and wherein the respective inwardly facing surface and outwardly facing surface are tapered at an angle relative to the pivot axis;
    a tubular member having first and second opposing ends and a lumen therethrough for receiving a guidewire, wherein the second end of the tubular member includes an outer diameter configured to be received within the opening in the second shank.

2. The surgical clamp system of claim 1, wherein the distal jaw portion of the first shank defines an opening therethrough.

3. The surgical clamp system of claim 1, wherein the distal jaw portion of the first shank comprises a clamping jaw and wherein the distal jaw portion of the second shank comprises a clamping jaw.

4. The surgical clamp system of claim 3, wherein the first and second jaw portions are aligned along a plane parallel to the distal jaw portion of the first and second shanks.

5. The surgical clamp system of claim 4, wherein each jaw portion includes a polygonal body.

6. The surgical clamp system of claim 1, wherein the angle is about 20 degrees.

7. The surgical clamp system of claim 1, wherein each inwardly facing surface includes a textured surface.

8. The surgical clamp system of claim 7, wherein the textured surface includes a serrated or knurled surface.

9. The surgical clamp system of claim 1, wherein the first and second shanks pivot about a rotation axis, and wherein each distal jaw portion is bent in a plane orthogonal to the rotation axis.

10. The surgical clamp system of claim 1, wherein the first and second shanks pivot about a rotation axis, and wherein each distal jaw portion is bent out of the plane orthogonal to the rotation axis of the main pivot joint.

11. The surgical clamp system of claim 1, wherein each distal jaw portion is fixed with respect to its respective shank.

12. The surgical forceps of claim 1, further comprising a hard stop arranged to prevent the distal jaw portions of the first and second shanks from touching one another.

* * * * *